United States Patent
Joye et al.

(10) Patent No.: US 6,428,534 B1
(45) Date of Patent: Aug. 6, 2002

(54) CRYOGENIC ANGIOPLASTY CATHETER

(75) Inventors: James Joye, Los Gatos; Richard S. Williams, Redwood City; Ronald Williams, Menlo Park, all of CA (US)

(73) Assignee: Cryovascular Systems, Inc., Los Gatos, CA (US)

( * ) Notice: Subject to any disclaimer, the term of this patent is extended or adjusted under 35 U.S.C. 154(b) by 0 days.

(21) Appl. No.: 09/510,903

(22) Filed: Feb. 23, 2000

Related U.S. Application Data

(60) Provisional application No. 60/121,638, filed on Feb. 24, 1999.

(51) Int. Cl.[7] .............................................. A61B 18/18
(52) U.S. Cl. ............................ 606/21; 606/22; 607/105
(58) Field of Search ............................ 606/20–23, 192, 606/194, 26; 607/104, 105

(56) References Cited

U.S. PATENT DOCUMENTS

| | | |
|---|---|---|
| 3,901,241 A | 8/1975 | Allen, Jr. |
| 4,336,691 A | 6/1982 | Burnstein et al. |
| 4,754,752 A | 7/1988 | Ginsburg et al. |
| 5,019,075 A | 5/1991 | Spears et al. |
| 5,041,089 A | 8/1991 | Mueller et al. |
| 5,078,713 A | 1/1992 | Varney |
| 5,092,841 A | 3/1992 | Spears |
| 5,106,360 A | 4/1992 | Ishiwara et al. |
| 5,147,355 A | 9/1992 | Friedman et al. |
| 5,151,100 A | 9/1992 | Abele et al. |
| 5,190,539 A | 3/1993 | Fletcher et al. |
| 5,191,883 A | 3/1993 | Lennox et al. |
| 5,196,024 A | 3/1993 | Barath |
| 5,275,595 A | 1/1994 | Dobak, III |
| 5,458,612 A | 10/1995 | Chin |
| 5,486,208 A | 1/1996 | Ginsburg |
| 5,501,681 A | 3/1996 | Neuwirth et al. |
| 5,545,195 A | 8/1996 | Lennox et al. |
| 5,617,739 A | 4/1997 | Little |
| 5,624,392 A | 4/1997 | Saab |
| 5,644,502 A | 7/1997 | Little |
| 5,733,280 A | 3/1998 | Avitall |
| 5,868,735 A | 2/1999 | Lafontaine |
| 5,899,898 A | 5/1999 | Arless et al. |
| 5,899,899 A | 5/1999 | Arless et al. |
| 5,902,299 A | 5/1999 | Jayaraman |
| 5,971,979 A | 10/1999 | Joye et al. |
| 6,241,718 B1 | 6/2001 | Arless et al. |
| 6,290,696 B1 * | 9/2001 | Lafontaine .................. 606/21 |

FOREIGN PATENT DOCUMENTS

| | | |
|---|---|---|
| WO | WO 91/05528 | 5/1991 |
| WO | WO 98/37822 | 9/1998 |
| WO | WO 98/38934 | 9/1998 |
| WO | WO 01/64145 A1 | 9/2001 |

OTHER PUBLICATIONS

U.S. patent application No. 09/203,011, filed on Dec. 1, 1998 entitled: *Apparatus and Method for Cryogenic Inhibiton of Hyperplasia*, Inventor(s): James Joye et al.

* cited by examiner

*Primary Examiner*—Roy D. Gibson
(74) *Attorney, Agent, or Firm*—Townsend and Townsend & CrewLLP; Mark D. Barrish, Esq.

(57) ABSTRACT

The invention provides techniques and devices for treating atherosclerotic disease using controlled cryogenic cooling, often in combination with angioplasty. The efficacy of endoluminal cryogenic cooling is enhanced by limiting cooling of target tissues using an insulated cryogenic balloon, the insulation ideally comprising a fluid which undergoes a phase change at a predetermined temperature. A combination cryogenic/angioplasty catheter avoids exchange procedures between dilation of a stenotic region within a vessel wall and the application of cryogenic cooling. The combination angioplasty/cryogenic cooling catheter may cool the diseased blood vessel before, during, and/or after dilation. Controlled cooling of the vessel wall may change its mechanical properties, weakening the vessel and allowing it to be expanded at a much lower pressure than with conventional uncooled angioplasty.

28 Claims, 4 Drawing Sheets

Expansion of N₂O from 500 psi and 0C

| Starting Conditions | | | | | | Final Conditions | | | | |
|---|---|---|---|---|---|---|---|---|---|---|
| Press (kPa) | Press (psia) | Temp (C) | Temp (K) | Density kgmole/m3 | Vapor (%) | Press (kPa) | Press (psia) | Temp (K) | Temp (C) | Vapor (%) |
| 3447 | 500 | 0 | 273.18 | 20.62 | 0 | 101.325 | 14.696 | 184.59 | -88.59 | 44.03 |
| 3447 | 500 | 0 | 273.18 | 20.62 | 0 | 137.9 | 20 | 189.92 | -83.26 | 42.35 |
| 3447 | 500 | 0 | 273.18 | 20.62 | 0 | 172.4 | 25 | 194.01 | -79.17 | 41.03 |
| 3447 | 500 | 0 | 273.18 | 20.62 | 0 | 206.8 | 30 | 197.50 | -75.68 | 39.87 |
| 3447 | 500 | 0 | 273.18 | 20.62 | 0 | 275.8 | 40 | 203.33 | -69.85 | 37.89 |
| 3447 | 500 | 0 | 273.18 | 20.62 | 0 | 344.7 | 50 | 208.12 | -65.06 | 36.19 |
| 3447 | 500 | 0 | 273.18 | 20.62 | 0 | 413.7 | 60 | 212.23 | -60.95 | 34.68 |
| 3447 | 500 | 0 | 273.18 | 20.62 | 0 | 482.6 | 70 | 215.86 | -57.32 | 33.32 |
| 3447 | 500 | 0 | 273.18 | 20.62 | 0 | 551.6 | 80 | 219.12 | -54.06 | 32.05 |
| 3447 | 500 | 0 | 273.18 | 20.62 | 0 | 620.5 | 90 | 222.09 | -51.09 | 30.87 |
| 3447 | 500 | 0 | 273.18 | 20.62 | 0 | 689.5 | 100 | 224.83 | -48.35 | 29.74 |

CRYOGENIC ANGIOPLASTY CATHETER

CROSS-REFERENCES TO RELATED APPLICATIONS

The present application claims the benefit of priority from U.S. patent application Ser. No. 60/121,638 filed Feb. 24, 1999 (Attorney Docket No. 18468-000400),the full disclosure of which is incorporated herein by reference.

BACKGROUND OF THE INVENTION

1. Field of the Invention

The present invention relates generally to apparatus and methods for treating atherosclerotic disease. In a particular embodiment, the present invention provides a combination of controlled cryogenic cooling and balloon distention of a diseased vessel wall.

A number of percutaneous intravascular procedures have been developed for treating atherosclerotic disease in a patient's vasculature. The most successful of these treatments is percutaneous transluminal angioplasty (PTA). PTA employs a catheter having an expansible distal end (usually in the form of an inflatable balloon) to dilate a stenotic region in the vasculature to restore adequate blood flow beyond the stenosis. Other procedures for opening stenotic regions include directional arthrectomy, rotational arthrectomy, laser angioplasty, stenting, and the like. While these procedures have gained wide acceptance (either alone or in combination, particularly PTA in combination with stenting), they continue to suffer from significant disadvantages. A particularly common disadvantage with PTA and other known procedures for opening stenotic regions is the subsequent occurrence of restenosis.

Restenosis refers to the re-narrowing of an artery following an initially successful angioplasty or other primary treatment. Restenosis typically occurs within weeks or months of the primary procedure, and may affect up to 50% of all angioplasty patients to some extent. Restenosis results at least in part from smooth muscle cell proliferation in response to the injury caused by the primary treatment. This cell proliferation is referred to as "hyperplasia." Blood vessels in which significant restenosis occurs will typically require further treatment.

A number of strategies have been proposed to treat hyperplasia and reduce restenosis. Previously proposed strategies include prolonged balloon inflation, treatment of the blood vessel with a heated balloon, treatment of the blood vessel with radiation, the administration of antithrombotic drugs following the primary treatment, stenting of the region following the primary treatment, and the like. While these proposals have enjoyed varying levels of success, no one of these procedures is proven to be entirely successful in avoiding all occurrences of restenosis and hyperplasia.

It has recently been proposed to prevent or slow reclosure of a lesion following angioplasty by remodeling the lesion using a combination of dilation and cryogenic cooling. Co-pending U.S. patent application Ser. No. 09/203,011, filed Dec. 1, 1998 (Attorney Docket No. 18468-000110), the full disclosure of which is incorporated herein by reference, describes an exemplary structure and method for inhibiting restenosis using a cryogenically cooled balloon. While these proposals appear promising, the described structures and methods for carrying out endovascular cryogenic cooling would benefit from still further improvements. For example, the mechanical strength of the vasculature generally requires quite a high pressure to dilate the vessel during conventional angioplasty. Conventional angioplasty often involves the inflation of an angioplasty balloon with a pressure of roughly 10 bar. These relatively high pressures can be safely used within the body when balloons are inflated with a benign liquid such as contrast or saline. However, high pressures involve some risk of significant injury should the balloon fail to contain a cryogenic gas or liquid/gas combination at these high pressures. Additionally, work in connection with the present invention has shown that the antiproliferative efficacy of endoluminal cryogenic systems can be quite sensitive to the temperature to which the tissues are cooled: although commercially available, cryogenic cooling fluids show great promise for endovascular use, it can be challenging to reproducibly effect controlled cooling without having to resort to complex, high pressure, tight tolerance, and/or expensive cryogenic control components.

For these reasons, it would be desirable to provide improved devices, system, and methods for treatment of diseased blood vessels. It would be further desirable if these improved techniques were compatible with known methods for treating atherosclerotic disease, but reduced the occurrence and/or extent of restenosis due to hyperplasia. It would be particularly desirable if these improved techniques were capable of delivering treatment in a very safe and controlled manner so as to avoid injury to adjacent tissues. These devices, systems, and methods should ideally also inhibit hyperplasia and/or neoplasia in the target tissue with minimum side effects, and without requiring a complex control system or making a physician introduce numerous different treatment structures into the target area. At least some of these objections will be met by the invention described hereinafter.

2. Description of the Background Art

A cryoplasty device and method are described in WO 98/38934. Balloon catheters for intravascular cooling or heating of a patient are described in U.S. Pat. No. 5,486,208 and WO 91/05528. A cryosurgical probe with an inflatable bladder for performing intrauterine ablation is described in U.S. Pat. No. 5,501,681. Cryosurgical probes relying on Joule-Thomson cooling are described in U.S. Pat. Nos. 5,275,595; 5,190,539; 5,147,355; 5,078,713; and 3,901,241. Catheters with heated balloons for post-angioplasty and other treatments are described in U.S. Pat. Nos. 5,196,024; 5,191,883; 5,151,100; 5,106,360; 5,092,841; 5,041,089; 5,019,075; and 4,754,752. Cryogenic fluid sources are described in U.S. Pat. Nos. 5,644,502; 5,617,739; and 4,336,691. The following U.S. Patents may also be relevant to the present invention: U.S. Pat. Nos. 5,458,612; 5,545,195; and 5,733,280.

The full disclosures of each of the above U.S. patents are incorporated by reference.

SUMMARY OF THE INVENTION

The present invention provides new techniques for treating atherosclerotic disease using controlled cryogenic cooling. The invention may be used as a combination cryogenic/angioplasty catheter, eliminating any need for an exchange procedure to be preformed between dilation of a stenotic region within a vessel wall and the application of cryogenic cooling to inhibit hyperplasia. The cooling catheter may be suitable for cooling the diseased blood vessel before, during, and/or after dilation. Advantageously, controlled cooling of the vessel wall changes its mechanical properties so as to enhance the ease of concurrent and/or subsequent dilation. Cooling and tissue temperatures can be accurately controlled by transferring heat from the vessel wall to a cryogenic fluid through a fluid having a predetermined phase change temperature. The change in phase of this heat-transfer fluid can repeatably limit the cooling catheter (and tissue) to a minimum treatment temperature. The use of a rigid heat exchanger within the dilation balloon enhances containment (and safety) of the cryogenic system.

In a first aspect, the invention provides a temperature-controlled cryogenic surgical system comprising a shaft having a proximal end and a distal end. A heat exchanger is disposed near the distal end of the shaft. A cryogenic fluid supply is in fluid communication with the heat exchanger. Fluid is disposed between the heat exchanger and a tissue engaging surface so as to limit heat transfer therebetween.

Typically, the fluid limits cooling of the tissue engaging surface by changing phase at a predetermined temperature. For example, the fluid may comprise saline having a salinity in the range from about 6% to about 18%, providing a treatment temperature in a range from about −5° C. to about −15° C. In the exemplary embodiment, the tissue engaging surface comprises an outer surface of a balloon, and the saline solution is used to inflate the balloon and limit a minimum tissue temperature using the latent heat of freezing, as the partially frozen saline within the balloon will remain substantially uniformly at the freezing temperature until completely frozen.

In another aspect, the invention provides a temperature-controlled cryogenic surgical catheter for use in a blood vessel of a patient body. The catheter comprises a flexible catheter body having a proximal end and a distal end. The body contains a cryogenic fluid supply lumen, an exhaust lumen, and a balloon inflation lumen. An inexpansible heat exchanger tube is disposed near the distal end of the body in fluid communication with the cryogenic fluid supply lumen and the exhaust lumen. A balloon containing the heat exchanger is in fluid communication with the inflation lumen, the balloon having a balloon wall. A balloon inflation fluid having a predetermined phase change temperature is disposed within the balloon between the heat exchanger and the balloon wall.

In another aspect, the invention provides a controlled cryosurgical method comprising positioning a balloon within a diseased portion of a blood vessel. The balloon is inflated with an inflation fluid having a predetermined phase change temperature. The diseased portion of the blood vessel is cooled by cryogenically cooling the inflation fluid to the predetermined phase change temperature. Preferably, the predetermined phase change temperature limits a minimum temperature of the diseased vessel wall to between about −5° C. and −15° C.

In another aspect, the present invention provides a system for treatment of a blood vessel having a diseased vessel wall. The system comprises a catheter body having a proximal end and a distal end and defining an axis therebetween. At least one balloon is disposed at the distal end of the body so that the at least one balloon can be positioned within the blood vessel adjacent the diseased vessel wall. The at least one balloon has an outer surface, and an angioplasty pressurization system is coupled to the proximal end of the body for balloon distention of the diseased vessel wall. A cooling fluid system is coupled to the proximal end of the body for cooling the diseased vessel wall. Thermal insulation is disposed between the cooling system and the outer surface of the balloon so as to limit cooling of the diseased vessel wall.

The thermal insulation may comprise a composition having a predetermined phase change temperature, as described above. Alternatively, the insulation may comprise a coating of a suitable material disposed on an inner or outer surface of the balloon, ideally being disposed between two nested balloon walls. Suitable insulation materials include expanded Teflon™ (ePTFE). Typically, both an angioplasty balloon and a cryogenic balloon will be included near the distal end of the catheter body, so that the characteristics of these two different structures can be optimized for their intended use. The catheter body generally includes an angioplasty lumen and one or more cryogenic fluid lumens to provide fluid communication between the pressurization and cooling systems and their associated balloon structures. In some embodiments, the balloons may be nested one inside the other (the cryogenic balloon preferably being disposed within the angioplasty balloon). Dilation may then be effected as with a standard angioplasty system, for example, by inflating the angioplasty balloon with a high contrast liquid. Cryogenic cooling of the vessel wall at the site of dilation may be performed before, during, and/or after expanding the vessel by introducing a cryogenic cooling fluid through the catheter body and into the nested cryogenic balloon. Optionally, the high contrast liquid within the angioplasty balloon may be at least partially evacuated during inflation of the nested cryogenic balloon, making it easier for the cryogenic fluid to inflate the cooling balloon and enhancing thermal coupling between the cooling fluid and the diseased vessel wall. Advantageously, the surrounding angioplasty balloon also acts as a safety mechanism, containing any exhaust gases which might escape from the cryogenic balloon. In an alternative embodiment, the angioplasty and cryogenic balloons may be axially displaced from each other.

In yet another aspect, the invention provides a system for treatment of a blood vessel having a diseased vessel wall. The system comprises a catheter body having a proximal end and a distal end and defining an axis therebetween. An angioplasty balloon is disposed at a first axial position on the body for positioning within the blood vessel adjacent the diseased vessel wall. A cryogenic balloon is disposed at a second axial position on the body.

In another aspect, the invention provides a system for treatment of a blood vessel having a diseased vessel wall. The system comprises a catheter body having a proximal end and a distal end and defining an axis therebetween. At least one balloon is disposed at the distal end of the body for positioning within the blood vessel adjacent the diseased vessel wall. An angioplasty pressurization system is coupled to the proximal end of the body for balloon distention of the diseased vessel wall. A cooling fluid system is coupled to the proximal end of the body for cooling the diseased vessel wall. A controller is operatively coupled to at least one of the pressurization system and the cooling system so as to coordinate distention of the diseased vessel wall with cooling of the diseased vessel wall.

In another aspect, the invention provides a catheter for treatment of a blood vessel having a diseased vessel wall. The catheter comprises a catheter body having a proximal end and a distal end. The body contains an angioplasty pressurization lumen, a cryogenic fluid supply lumen, and a cryogenic fluid exhaust lumen. An angioplasty balloon is disposed near the distal end of the body. The angioplasty balloon is in fluid communication with the pressurization lumen, and is capable of dilating the diseased vessel wall when the angioplasty balloon is pressurized within the blood vessel. A cryogenic balloon is also disposed near the distal end of the body. The cryogenic balloon is in fluid communication with the exhaust lumen. A diffuser having a plurality of cryogenic fluid ports is disposed within the cryogenic balloon. The supply lumen is in fluid communication with the balloon through the diffuser so that cryogenic fluid from the supply lumen is distributed within the balloon by the diffuser.

In each of these devices, systems, and methods, a stent may optionally be placed over the balloon so that the stent can be deployed within the body lumen. Cooling may be effected before or during deployment of the stent, and will preferably be effected after the stent is deployed using the balloon.

DESCRIPTION OF THE SPECIFIC EMBODIMENTS

The devices, systems, and methods of the present invention are related to co-pending U.S. patent application Ser. No. 09/203,011, filed on Dec. 1, 1998 for an Apparatus and Method for Cryogenic Inhibition of Hyperplasia. That application is assigned to the present assignee, and its full disclosure is incorporated herein by reference.

Figure 1:
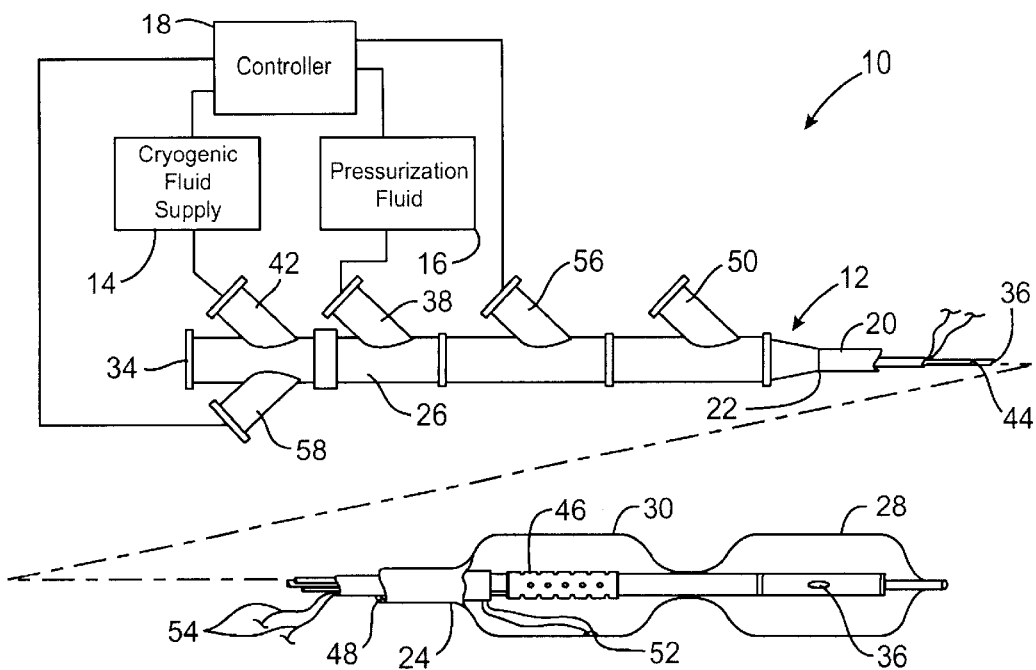
FIG. 1 schematically illustrates a combined cryogenic/angioplasty system including a catheter with an angioplasty balloon that is axially displaced from a cryogenic balloon.

Referring now to FIG. 1, an exemplary system 10 is capable of treating a diseased vessel wall of a blood vessel using a combination of both angioplasty dilation and cryogenic cooling. In general, system 10 includes a catheter 12 coupled to a cryogenic fluid supply system 14 and an angioplasty pressurization system 16. One or both of cryogenic system 14 and pressurization system 16 may be operatively coupled to a controller 18 for coordination of cooling and dilation, as will be described in more detail hereinbelow.

Catheter 12 generally includes a catheter body 20 having a proximal end 22 and a distal end 24. A proximal housing 26 includes a number of ports for coupling of cryogenic system 14, pressurization system 16, and the like to the proximal end of the catheter body. An angioplasty balloon 28 and a cryogenic balloon 30 are mounted near the distal end 24 of catheter body 20. The catheter body will generally be flexible and contain a plurality of lumens to provide fluid communication between the ports of proximal housing 26 and balloons 28 and 30.

Angioplasty balloon 28 may be formed from a variety of materials conventionally used for dilating blood vessels. Angioplasty balloon 28 will typically comprise a nondistensible material such as polyethylene terephthalate (PET). Such angioplasty balloons are formed in a variety of sizes depending on their intended use, typically having a length in a range from about 15 mm to about 50 mm and an expanded diameter in a range from about 2 mm to about 10 mm. Prior to inflation, angioplasty balloon 28 will generally remain in a low profile configuration suitable for insertion into and maneuvering through the vascular system. A guidewire lumen 32 extends through angioplasty balloon 28 and cryogenic balloon 30 from a proximal guidewire port 34 to facilitate accessing the target treatment site.

Angioplasty balloon 28 is inflated by injecting fluid from pressurization system 16 into a pressurization lumen 36 through a pressurization port 38. In the embodiment of FIG. 1, balloon 28 will preferably be isolated from balloon 30, so as to avoid inadvertent inflation of the cryogenic balloon during dilation. High contrast markers may be provided within the balloon to enhance an image of the distal end of the catheter and facilitate positioning of the balloon fluoroscopically, sonographically, or under any other alternative image modality (with appropriate contrast structures). Such markers may be formed by winding a gold or platinum wire around the tubular structure defining pressurization lumen 36, as illustrated.

In the embodiment of FIG. 1, cryogenic balloon 30 is disposed proximally of angioplasty balloon 28. This arrangement is advantageous for first at least partially dilating the vessel wall and then treating the dilated vessel wall with cryogenic cooling, which can facilitate positioning of the cryogenic balloon within an occluded region of the vessel. In alternative embodiments, the cryogenic balloon may be disposed distally of the angioplasty balloon.

Figure 2:
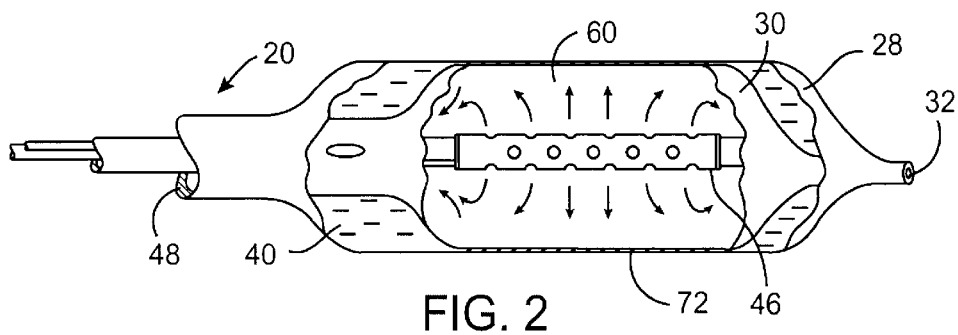
FIG. 2 illustrates an alternative distal end of the cryogenic/angioplasty catheter for use in the system of FIG. 1, in which a cryogenic balloon is nested within an angioplasty balloon.

The structure and operation of cryogenic balloon 30 may be understood with reference to FIGS. 1 and 2, and also with reference to U.S. patent application Ser. No. 09/203,011, previously incorporated herein by reference. Cryogenic fluid will often be injected into a cryogenic supply port 42 and passed toward cryogenic balloon 30 through cryogenic supply lumen 44 within catheter body 20. Cryogenic fluid may comprise cryogenic liquids or liquid/gas mixtures, optionally including carbon dioxide, nitrous oxide, liquid nitrogen, or the like. As the cryogenic liquid passes from supply lumen 44 and into cryogenic balloon 30, it is preferably distributed both radially and axially by a diffuser 46. Diffuser 46 will generally comprise a tubular structure with radially oriented openings. As the openings are radially oriented, diffuser 46 will direct the cooling fluid roughly perpendicularly against the wall of cryogenic balloon 30, so that the heat transfer coefficient between the cooling vapor and balloon wall is quite even and quite high. This helps to reduce the temperature of the balloon wall and provides greater heat extraction for a given flow rate of coolant into the balloon. Additionally, as the ports of diffuser 46 are distributed both circumferentially and axially along the balloon, the diffuser can provide a substantially uniform cooling over a significant portion of (often over the majority of) the surface of the balloon.

In some embodiments, the cryogenic cooling fluid may pass through a Joule-Thomson orifice between fluid supply lumen 44 and balloon 30. In other embodiments, at least a portion of the cryogenic cooling fluid may exit one or more ports into the balloon as a liquid. The liquid will vaporize within the balloon, and the enthalpy of vaporization can help cool the surrounding vessel wall. The liquid may coat at least a portion of the balloon wall so as to enhance even cooling over at least a portion of the vessel wall. Hence, the ports of diffuser 46 may have a total cross-section which is smaller than a cross-section of the fluid supply of lumen 44, or which is at least as large as (or larger than) the cross-section of the fluid supply lumen.

After the cryogenic cooling fluid vaporizes within balloon 30, it escapes the balloon proximally along an exhaust lumen 48 and is exhausted from catheter 12 through an exhaust port 50. Inflation of cryogenic balloon 30 may be controlled by the amount of cryogenic fluid injected into the balloon, and/or by the pressure head loss experience by the exhaust gases. Cooling is generally enhanced by minimizing the pressure within balloon 30. To take advantage of this effect so as to control the amount of cooling a fixed or variable orifice may be provided at exhaust port 50. Alternatively, a vacuum may be applied to the exhaust port to control cooling and enhance cooling efficiency.

An exemplary structure for diffuser 46 may comprise a polyimide tube having an inner diameter of about 0.032 inches and a wall thickness of 0.001 inch. Each port will define a diameter of about 0.0025 inches. There will typically be between six and six hundred ports in diffuser 46. In the exemplary embodiment, four axial rows of ports are separated by about 90° from each other. The rows are axially staggered so that the ports in a single row have central line separations of about 4 mm, while the ports of adjacent rows are separated by about 2 mm. The overall length of the porous diffuser tube will vary with the length of the balloon, and will typically be about 2 cm.

Diffuser 46 may be bonded concentrically about a central shaft defining guidewire lumen 32. Adhesives seal the proximal and distal ends of the diffuser, or the diffuser can be incorporated at the distal end of tube 64 with an adhesive seal at the distal end of the diffuser. High contrast markers may again be provided to enhance an image of the catheter and facilitate positioning of cryogenic balloon 18 at the treatment site. The cryogenic cooling fluid will generally be introduced through the annular space between the diffuser tube and the central shaft proximally of the balloon. The central shaft will typically comprise a polyimide tube, but may alternatively include any of a wide variety of materials.

In some embodiments, a temperature sensor may be thermally coupled to balloon 30 to monitor and/or control cryogenic cooling of the arterial wall. Temperature sensor 52 may optionally be disposed on an inner or outer surface of balloon 30, and is coupled to controller 18 by thermocouple leads 54. Temperature sensor 52 may comprise a thermocouple, thermistor, or the like.

To inhibit restenosis, controller 18 will generally initiate, monitor, and/or control cooling of the tissue. Cryogenic supply 14 will often inject sufficient cryogenic cooling fluid to effect a cooling rate of the tissue in a range from about 2° C. to about 30° C. per second. In an exemplary treatment, the system will maintain the temperature in a range from about 0° C. to about −80° C., optionally at a temperature in range from −5° C. to about −40° C., for a time between about 1 and 60 seconds, ideally maintaining the tissue at a temperature in a range from about −5° C. to about −15° C. for a time from about 10 to about 30 seconds. The efficacy of the therapy at inhibiting restenosis may be enhanced by repeatedly cooling the tissue to such temperatures for between 1 and 5 cooling cycles, typically repeating these cycles at a rate of between about 1 and 6 cooling cycles every 60 seconds. Typical treatment cycles may cool a surface temperature of the endothelium down to about −10° C., then allow the surface temperature to warm to about 0° C. For example, five of these cooling cycles might be performed in about 40 seconds. To provide cooling, a cryogenic liquid or liquid/gas mixture comprising carbon dioxide, nitrous oxide, or the like may flow through the balloon at a rate in an average from about 100 to about 800 mg per second. Such cooling (and optional cooling cycles) may induce apoptosis, cell membrane damage, and/or programmed cell death.

To accurately control and/or monitor the pressure within cryogenic balloon 30, proximal housing 26 may include a cooling balloon pressure monitoring port 56. The pressure monitoring port will be in fluid communication with the cryogenic balloon 30, preferably through a dedicated pressure monitoring lumen (not shown). Signals from pressure monitoring port 56 and a thermal couple connector 58 may be transmitted to the controller 18. This allows the use of a feedback control system for initiating, regulating, and halting the supply of cryogenic fluid from fluid supply system 14. More specifically, the controller will often provide a control signal to the fluid supply system in response to signals from pressure monitoring port 56 and/or thermal couple connector 58.

Referring now to FIG. 2, an alternative combination cryogenic/angioplasty catheter again includes both a cryogenic balloon 30 and an angioplasty balloon 28. In this embodiment, cryogenic balloon 30 is nested within angioplasty balloon 28, so that if the low pressure cooling balloon were to break during the procedure, the higher pressure capability of the surrounding angioplasty balloon 28 would contain the exhaust gases until the flow of coolant was stopped. In other respects, the structure of this nested embodiment is quite similar to that described above.

In use, the nested cryogenic/angioplasty balloon catheter of FIG. 2 may allow pre-cooling of a diseased vessel wall prior to dilation, cooling of a vessel wall after dilation, interspersed cooling/dilation, and even concurrent dilation during cooling. Advantageously, the catheter need not be repositioned between the application of dilation pressure and cryogenic cooling. Hence, this nested embodiment facilitates the immediate sequential pre- and/or post-cooling of the stenosed vessel wall, thereby giving a wide flexibility in the treatment protocol. Advantageously, the interaction of cooling and dilation may be precisely prescribed and effected by controller 18 (see FIG. 1) without having to wait for the operator to reposition the catheter.

Where the vessel wall is to be at least partially dilated prior to cryogenic cooling, angioplasty balloon 28 may be inflated first with contrast liquid 40 (as used in conventional angioplasty). The contrast liquid may then be at least partially evacuated, allowing cooling balloon 30 to be inflated at a pressure that is lower than the angioplasty distention pressure. Inflation of cryogenic balloon 30 pushes the angioplasty balloon against the diseased wall of the vessel, so that the cryogenic fluid 60 within the cryogenic balloon is thermally coupled to the diseased vessel wall by both the cryogenic balloon wall and the angioplasty balloon wall in series. To enhance heat flow through the balloon walls, a heat transfer enhancing material may be included in cryogenic balloon 30 and/or angioplasty balloon 28, particularly where treatment temperatures of about −50° C. and below are desired. For example, the addition of between about 1% and 10% boron nitride in a polyethylene or other balloon polymer can significantly improve heat transfer of the entire system. Surprisingly, a significant temperature differential may be found between an inner and outer surface of each balloon during cooling. Hence, improving the thermal conductivity of each balloon wall disposed between cryogenic fluid 60 and the targeted wall of the vessel may provide significant benefits when cooling to low temperatures.

In alternative methods for using the nested cryogenic/angioplasty balloon of FIG. 2, cooling may be initiated prior to complete dilation of the stenosed region of the vessel. The cooling process changes the mechanical properties of the vessel and allows it to be expanded or dilated at a much lower pressure than is used with conventional angioplasty. For example, dilation of a cryogenically cooled vessel may require inflation of angioplasty balloon 28 with a fluid pressure of about 2 bar, as compared to about 10 bar for conventional uncooled angioplasty on the same vessel wall. Simultaneous cryogenic cooling and angioplasty may reduce and/or eliminate medial vessel fractures, thereby inhibiting proliferative response after angioplasty. It should be noted that at least some of these advantages may be provided by using a single balloon coupled to both a cryogenic supply system 14 and a pressurization system 16. Such a cooling/angioplasty catheter used in this fashion may allow the operator to perform both angioplasty and cryogenic antiproliferative treatments with a single inflation cycle of the balloon.

Still further alternative treatment cycles are possible, including inflating a balloon with a room temperature gas at normal angioplasty pressures to dilate the vessel, and then inflating the balloon with a cryogenic fluid or other coolant to treat the dilated area so as to inhibit hyperplasia. Alternatively, a balloon may be inflated with a standard angioplasty contrast liquid at normal angioplasty pressures to dilate the vessel. The balloon may then be flushed with saline, and then flushed with a dry room temperature gas to dry the cooling fluid path. After the cryogenic fluid path is dry, the balloon may be inflated with a coolant to treat the dilated area. Cooling cycles before angioplasty and/or before stenting may also provide the antiproliferative response described above.

Figure 3:
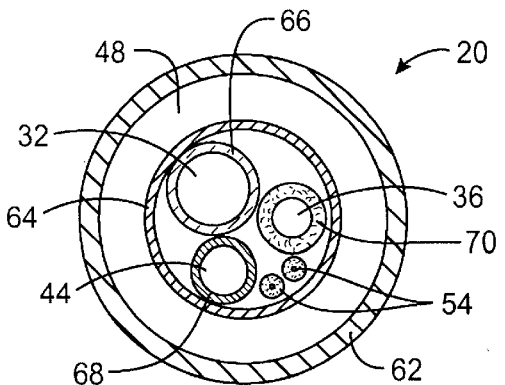
FIG. 3 is a cross-section taken along the catheter body of the cryogenic/angioplasty system of FIG. 1.

Referring now to FIG. 3, the structure of catheter body 20 is illustrated in cross-section. An outer sheath 62 partially defines exhaust lumen 48, the exhaust lumen here comprising an annular space disposed between the sheath and an inner jacket 64. In, the exemplary embodiment, sheath 62 comprises a polyethylene tube having an inner diameter of 0.058 inches and a wall thickness of about 0.003 inches. The exemplary jacket 64 comprises a polyimide having an inner diameter of 0.032 inches and a wall thickness of 0.001 inches.

Within jacket 64, a core shaft 66 defines guidewire lumen 32, while a cooling inlet tube 68 and an angioplasty pressurization tube 70 define supply lumen 44 and pressurization lumen 36, respectively. The exemplary cooling inlet tube comprises a polyester or polyimide, while the pressurization tube in the exemplary system may comprise a polyester or high density polyethylene. A wide variety of alternative materials might also be used. Thermocouple leads 54 are insulated in a conventional manner.

Figures 4A, 4B:
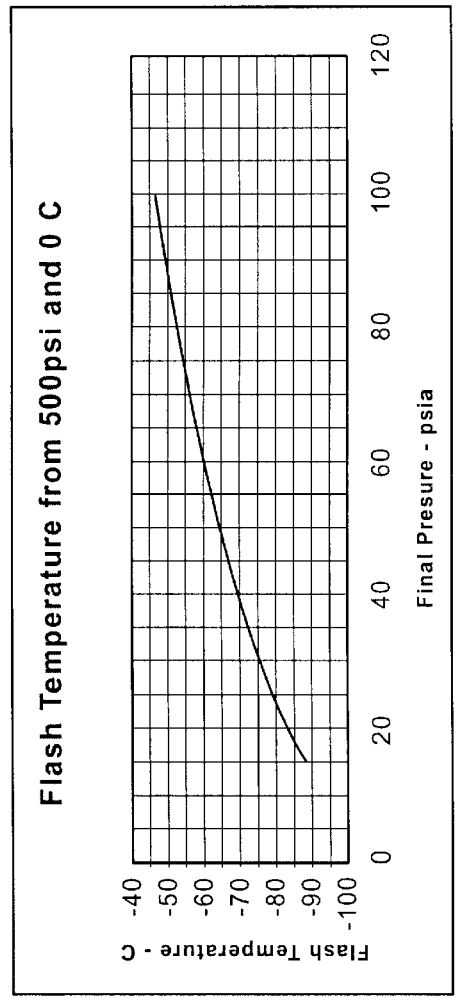
FIGS. 4A and 4B illustrate cryogenic cooling temperatures provided by expansion of $N_2O$.

The above discussion describes structures and techniques for enhancing the efficiency of cryogenic cooling within a blood vessel. However, cryogenic cooling is capable of inducing temperatures well below the preferred antiproliferative treatment ranges of the present invention (typically in a range from about −5° C. to about −15° C. ). Referring now to FIGS. 4A and B, expansion of $N_2O$ from an initial pressure of 500 psi and an initial temperature of 0° C. to final pressures in a range from atmospheric pressure to 100 psi results in a cryogenic cooling fluid temperature significantly colder than our preferred target tissue temperatures. As it may be convenient to make use of commercially available 500 psi $N_2O$, it may be beneficial to include an additional temperature control mechanism to provide our desired treatment temperatures. While it may be possible to maintain expanded cryogenic fluid pressures above 100 psi, the use of such high pressure gases within the vasculature may involve a significant risk of serious injury if the high pressure gases escape the catheter and enter the blood stream.

Referring once again to FIG. 2, one simple technique for reducing tissue cooling without increasing fluid within our balloon structures is to add a layer of insulating material 72 between the cryogenic cooling fluid and the tissue engaging surface of the balloon. A suitable insulation material might include a thin layer of expanded Teflon™ (ePTFE) on an inner or outer surface of cryogenic balloon 30, on an inner or outer surface of angioplasty balloon 28, or the like. The ePTFE layer may have a thickness in the range from about 0.00025 inches to about 0.001 inches. A wide variety of alternative insulation materials might also be used. Alternative active temperature control techniques might be used with or without such an insulation layer, including the use of controller 18 as shown in FIG. 1.

Figure 5:
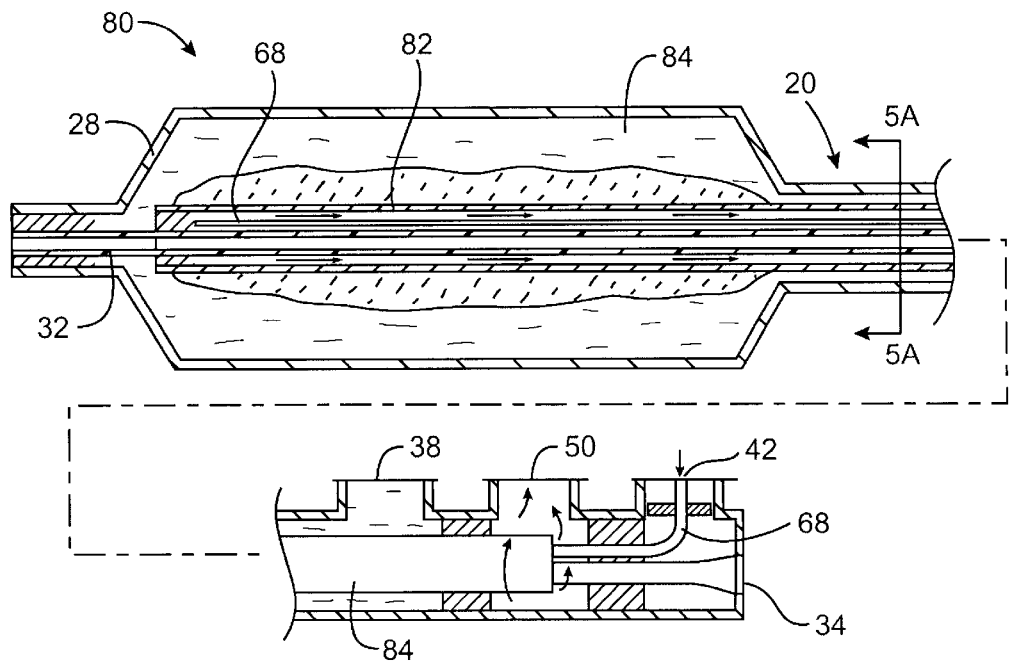
FIGS. 5 and 5A illustrate a particularly preferred controlled temperature cryogenic catheter in which a saline solution having a predetermined freezing temperature controls the cooling of tissues by thermally coupling an inexpansible heat exchanger with a surrounding angioplasty balloon.
Figure 5A:
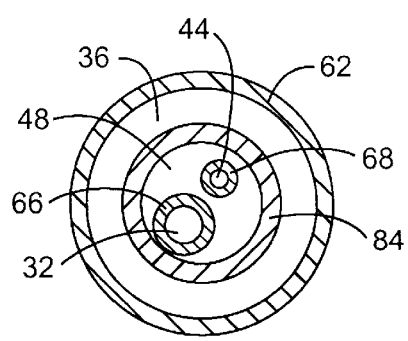

A particularly advantageous temperature control mechanism can be understood with reference to FIGS. 5 and 5A. In this embodiment, a controlled temperature cryogenic balloon catheter 80 again includes an angioplasty balloon 28, which here contains an inexpansible heat exchanger 82. Cooling of fluid inlet tube 68 releases the cryogenic cooling fluid within heat exchanger 82, but does not expand the heat exchanger into direct thermal contact with the balloon wall of angioplasty balloon 28. Instead, a saline solution 84 thermally couples the heat exchanger to the outer surface of angioplasty balloon 28.

Saline solution 84 will generally have a predetermined freezing temperature, and sufficient cryogenic cooling fluid will generally be provided to heat exchanger 82 so that the saline solution is only partially frozen. As a result, the temperature of the saline solution within angioplasty balloon 28 will be maintained accurately at the freezing temperature. As the freezing temperature of saline may be varied by changing the salinity, this provides a convenient control mechanism to vary the treatment temperature. Specifically, a 6% saline solution will freeze at about −3.5° C., while an 18% saline solution will freeze at about −14° C. By varying the salinity between about 6% and 18%, the temperature of the saline solution during cryogenic cooling (while the saline is partially frozen) can be selected within a range from about −5° C. to about −15° C. In an exemplary embodiment, a 12% saline solution will provide a freezing temperature of about −8° C, which is particularly advantageous for use with the controlled-temperature cryogenic catheter 80 illustrated in FIG. 5.

It should be understood that there may be a significant temperature difference between the freezing temperature of saline solution 84 and the surface temperature of the endothelium, and that this variation may depend on the particular angioplasty balloon structure used. Nonetheless, these controlled temperature cryogenic catheters can take advantage of the latent heat of freezing to provide an accurate treatment temperature despite minor variations in the cryogenic cooling flow, exhaust gas pressure due to bending of the catheter shaft, or the like.

It should be understood that a variety of fluids, and possibly even solids, might be used in place of saline solution 84. In general, temperature control will be provided where a thermally coupling structure undergoes a change in phase involving a significant latent phase change energy. Nonetheless, saline is particularly preferred as its range of freezing temperatures can be easily controlled within the desired range, and as it poses little risk in the event of release within the vasculature. Optionally, contrast may be included with the saline solution to improve imaging of the system within the patient body.

In the exemplary embodiment illustrated in FIGS. 5 and 5A, heat exchanger 82 extends proximally from angioplasty balloon 28 to at least in part define exhaust lumen 48. This simple proximal tubular structure (which is referred to herein as an evaporator 84) may comprise a polyimide tube having an inner diameter in a range from about 0.036 inches to about 0.051 inches, ideally having an inner diameter of about 0.045 inches. Cooling inlet tube 68 within evaporator 84 and heat exchanger 82 may comprise a polyimide tube having an inner diameter in a range from about 0.005 inches to about 0.012 inches, ideally having an inner diameter of about 0.009 inches.

It is possible that evaporator 84 extending the entire length of the catheter may cause sufficient cooling of the saline proximally of the angioplasty balloon to induce freezing along catheter body 20. To reduce this, an insulation jacket may be provided around the evaporator proximally of heat exchanger 82. The insulation jacket may comprise a polyimide tube, preferably leaving a gap (as small as 0.001 inches) between the insulation jacket wall and evaporator 84. Alternatively, the balloon inflation lumen may be altered to prevent the saline from thermally coupling exhaust lumen 48 to outer sheath 64. For example, a polyimide tube having an inner diameter in a range from about 0.012 inches to about 0.025 inches may be disposed between evaporator 84 and outer sheath 62, with this additional tubular structure providing fluid communication between inflation port 38 and angioplasty balloon 28. In either of these embodiments, an additional port may be provided on the proximal housing in communication with the insulation gap (either between the insulation jacket and evaporator 84 or between evaporator 84 and outer sheath 62) such that at least some of the air could be evacuated from this gap to reduce heat transfer to in the blood surrounding catheter body 20 and the exhaust gases.

Figure 6A:
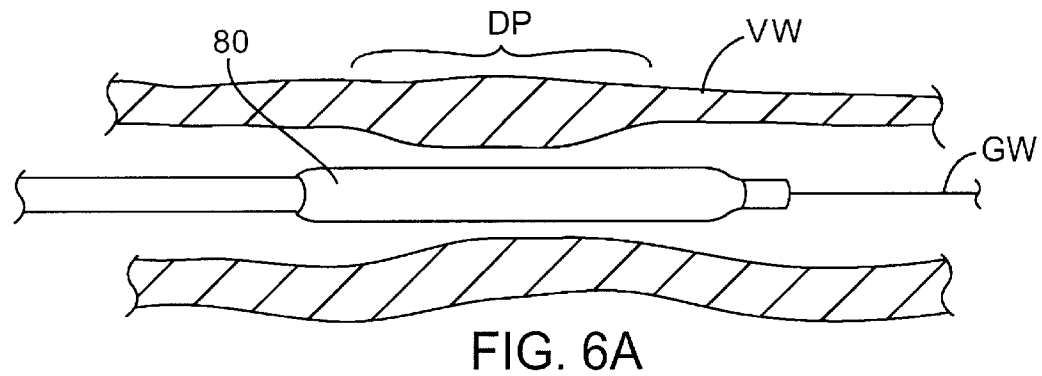
FIGS. 6A through C schematically illustrate a method for using the controlled temperature cryogenic balloon of FIG. 5.
Figure 6B:
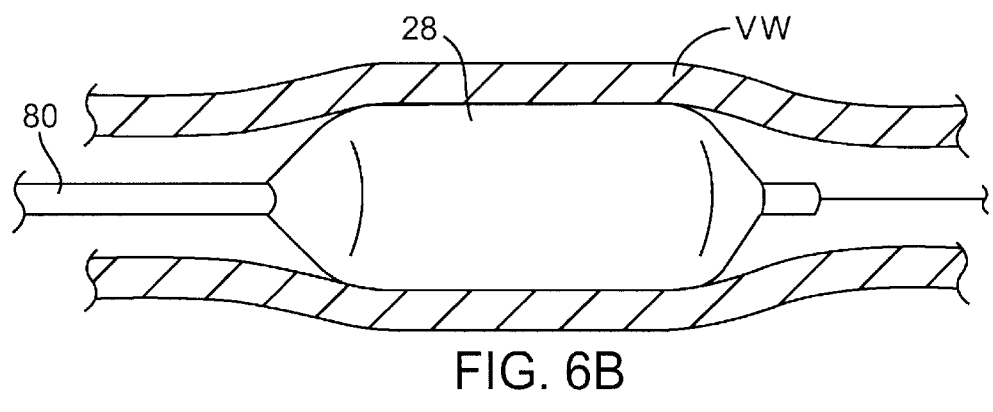
Figure 6C:
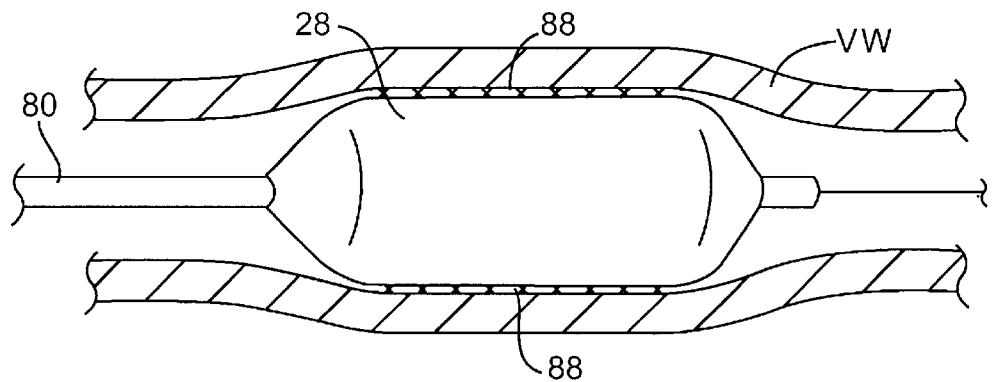

A method for using controlled-temperature cryogenic catheter 80 is illustrated in FIGS. 6A through C. Typically, the catheter is introduced into the vasculature through an introducer sheath, most often using the widely known Seldinger technique. A guide wire GW is maneuvered through the vessel, and catheter 80 is advanced over the guide wire and positioned adjacent diseased portion DP of vessel wall VW.

Once angioplasty balloon 28 is in position, the balloon may be inflated in a conventional manner through inflation port 38 to dilate the vessel, as illustrated in FIG. 6B. Optionally, the vessel may be dilated using conventional contrast fluid to facilitate fluoroscopically directing dilation. When standard contrast has been used for dilation, the balloon may be evacuated and filled with a saline solution which freezes at the desired treatment temperature. Alternatively, dilation may be performed using this saline solution to avoid any delay between dilation and cryogenic treatment. In still further alternative treatments, cryogenic cooling may be initiated prior to or during dilation. Regardless, prior to cooling the saline solution having the predetermined freezing temperature will preferably be used to inflate angioplasty balloon 28 with sufficient pressure to provide good contact between the balloon and vessel wall VW. Typically, the angioplasty balloon will be inflated by the saline solution to a pressure in a range from about 5 psi to about 30 psi, as illustrated in FIG. 6B.

To initiate cooling, a cryogenic fluid (usually in the form of a liquefied refrigerant or liquid/gas mixture) is injected into cryogenic supply port 42. The cryogenic fluid flows through fluid supply lumen 44 and is transmitted into heat exchanger 82, where it rapidly absorbs heat and vaporizes, thereby cooling saline 84 and angioplasty balloon 28. As the coolant vaporizes, it passes proximally along evaporator 84 to exhaust port 50. Sufficient cryogenic cooling fluid is supplied to partially freeze saline 84, so that the saline liquid/solid mixture remains at about freezing temperature. Optionally, additional cryogenic cooling fluid may be introduced, with the freezing of the saline providing a temporary plateau along the temperature excursion profile. More typically, the partially frozen saline melts by absorbing heat from the surrounding body. In the meantime, the cooling of saline within angioplasty balloon 28 results in treatment of a surface layer 88 of vessel wall VW engaged by the angioplasty balloon to an accurately controlled treatment temperature in a range from about −5° C. to about −15° C. As a result, this treated tissue layer undergoes apoptosis, thereby avoiding and/or reducing the proliferative response of the luminal wall to dilation.

While the exemplary embodiments have been described in some detail by way of example and for clarity of understanding, a variety of changes, adaptations, and modifications will be obvious to those of skill in the art. Hence, the scope of the present invention is limited solely by the appended claims.

What is claimed is:

1. A temperature-controlled cryogenic surgical system comprising:

a shaft having a proximal end and a distal end;

a heat exchanger disposed near the distal end of the shaft;

a cryogenic fluid supply in fluid communication with the heat exchanger;

a tissue engaging surface; and a fluid disposed between the heat exchanger and the tissue engaging surface so as to limit heat transfer therebetween, wherein the fluid limits cooling of the tissue engaging surface by changing phase at a predetermined temperature.

2. The temperature-controlled cryogenic surgical system of claim 1, wherein the fluid comprises saline.

3. The temperature-controlled cryogenic surgical system of claim 2, wherein the saline has a salinity in a range from about 6% to about 18% and freezes at a temperature in a range from about −5° C. to about −15° C.

4. A temperature-controlled cryogenic surgical system comprising:

a shaft having a proximal end and a distal end;

a heat exchanger disposed near the distal end of the shaft;

a cryogenic fluid supply in fluid communication with the heat exchange;

a tissue engaging surface; and a fluid disposed between the heat exchanger and the tissue engaging surface so as to limit heat transfer therebetween;

wherein the shaft comprises an axially flexible tubular body containing cryogenic fluid supply lumen and an exhaust lumen in fluid communication with the heat exchanger.

5. The temperature-controlled cryogenic surgical system of claim 4, wherein the tissue engaging surface comprises an outer surface of a balloon, the balloon expandable by the fluid to engage a surrounding vessel wall, the heat exchanger being disposed within the balloon and separating the cryogenic fluid supply and the inflation fluid.

6. The temperature-controlled cryogenic surgical system of claim 5, wherein the balloon comprises an angioplasty balloon, the heat exchanger comprising an inexpansible tube extending axially within the balloon.

7. A temperature-controlled cryogenic surgical catheter for use in a blood vessel of a patient body, the catheter comprising:
- a flexible catheter body having a proximal end and a distal end, the body containing a cryogenic fluid supply lumen, an exhaust lumen, and a balloon inflation lumen;
- an inexpansible heat exchanger tube disposed near the distal end of the body in fluid communication with the cryogenic fluid supply lumen and the exhaust lumen;
- a balloon containing the heat exchanger and in fluid communication with the inflation lumen, the balloon having a balloon wall; and
- a balloon inflation fluid having a predetermined freezing temperature disposed within the balloon between the beat exchanger and the balloon wall.

8. A controlled cryosurgical method comprising:
- positioning a balloon within a diseased portion of a blood vessel;
- inflating the balloon with an inflation fluid having a predetermined phase change temperature; and
- cooling the diseased portion of the blood vessel by cryogenically cooling the inflation fluid to the predetermined phase change temperature, wherein the inflation fluid is cooled with a cryogenic fluid through an inexpansible heat exchanger, wherein the heat exchanger is separated from a balloon wall of the balloon by the inflation fluid during the cooling step.

9. The cryosurgical method of claim 8, further comprising selecting a composition of the inflation fluid to define the predetermined phase change temperature.

10. The cryosurgical method of claim 9, wherein the selecting step comprises varying a salinity of a saline solution between about 6% and about 18%. the phase change temperature comprising the freezing temperature of the saline.

11. The cryosurgical method of claim 9, wherein the predetermined phase change temperature limits a minimum temperature of the diseased vessel wall to between about −5 and −15C.

12. The cryosurgical method of claim 9, wherein cooling further comprises supplying sufficient cryogenic cooling fluid to effect a change in phase of a portion of the inflation fluid so that the change in phase limits a minimum temperature of the inflation fluid to the predetermined phase change temperature.

13. A system for treatment of a blood vessel having a diseased vessel wall, the system comprising:
- a catheter body having a proximal end and a distal and defining an axis therebetween;
- at least one balloon disposed at the distal end of tho body for positioning within the blood vessel adjacent the diseased vessel wall, the at least one balloon having an outer surface;
- an angioplasty pressurization system coupled to the proximal end of the body for balloon distention of the diseased vessel wall;
- a cooling fluid system coupled to the proximal end of the body for cooling the diseased vessel wall; and
- a layer of insulating material disposed between the cooling system and the outer surface of the balloon so as to limit cooling of the diseased vessel.

14. A system for treatment of a blood vessel having a diseased vessel wall, the system comprising:
- a catheter body having a proximal end and a distal end and defining an axis therebetween;
- at least one balloon disposed at the distal end of the body for positioning within the blood vessel adjacent the diseased vessel wall, the at least one balloon having an outer surface;
- angioplasty pressurization system coupled to the proximal end of the body for balloon distention of the diseased vessel wall;
- a cooling fluid system coupled to the proximal end of the body for cooling the diseased vessel wall;
- thermal insulation disposed between the cooling system and the outer surface of the balloon so as to limit cooling of the diseased vessel; and
- an angioplasty balloon and a cryogenic balloon, the body containing an angioplasty lumen and at least one cryogenic fluid lumen, the angioplasty lumen providing fluid communication between the angioplasty balloon and the pressurization system, the at least one cryogenic fluid lumen providing fluid communication between the cryogenic fluid system and the cryogenic balloon.

15. The system of claim 14, wherein the cryogenic balloon is nested within the angioplasty balloon.

16. The system of claim 15, wherein the angioplasty pressurization system directs a high contrast liquid into the angioplasty balloon outside the cryogenic balloon.

17. A system for treatment of a blood vessel having a diseased vessel wall, the system comprising:
- a catheter body having a proximal end and a distal end and defining an axis therebetween;
- at least one balloon disposed at the distal end of the body for positioning within the blood vessel adjacent the diseased vessel wall, the at least one balloon having an outer surface;
- an angioplasty pressurization system coupled to the proximal end of the body for balloon distention of the diseased vessel wall;
- a cooling fluid system coupled to the proximal end of the body for cooling the diseased vessel wall; and
- thermal insulation disposed between the cooling system and the outer surface of the balloon so as to limit cooling of the diseased vessel, wherein the insulation comprises a composition having a predetermined phase change temperature.

18. A system for treatment of a blood vessel having a diseased vessel wall, the system comprising:
- a catheter body having a proximal end and a distal end and defining an axis therebetween;
- at least one balloon disposed at the distal end of the body for positioning within the blood vessel adjacent the diseased vessel wall, the at least one balloon having an outer surface;
- an angioplasty pressurization system coupled to the proximal end of the body for balloon distention of the diseased vessel wall;
- a cooling fluid system coupled to the proximal end of the body for cooling the diseased vessel wall; and
- thermal insulation disposed between the cooling system and the outer surface of the balloon so as to limit cooling of the diseased vessel wherein the insulation comprises a coating including ePTFE.

19. A system for treatment of a blood vessel having a diseased vessel wall, the system comprising:

a catheter body having a proximal end and a distal end and defining an axis therebetween;

an angioplasty balloon disposed at a first axial position on the body for positioning within the blood vessel adjacent the diseased vessel wall; and a cryogenic balloon disposed at a second axial position on the body.

20. The system of claim 19, wherein the cryogenic balloon is disposed proximally of the angioplasty balloon.

21. A system for treatment of a blood vessel having a diseased vessel wall, the system comprising:

a catheter body having a proximal end and a distal end and defining an axis therebetween;

at least one balloon disposed at the distal end of the body for positioning within the blood vessel adjacent the diseased vessel wall;

an angioplasty pressurization system coupled to the proximal end of the body for balloon distention of the diseased vessel wall;

a cooling fluid system coupled to the proximal end of the body for cooling the diseased vessel wall; and a controller operatively coupled to at least one of the pressurization system and the cooling system so as to coordinate distention of the diseased vessel wall with cooling of the diseased vessel wall.

22. The system of claim 21, wherein the controller effects concurrent cryogenic cooling and distention of the diseased vessel wall.

23. The system of claim 22, wherein the controller effects distention of the diseased vessel wall after initiation of cryogenic cooling of the diseased vessel wall.

24. The system of claim 23, wherein the controller effects pressurization of the angioplasty balloon with a pressure which is less than an uncooled vessel distention pressure.

25. A catheter for treatment of a blood vessel having a diseased vessel wall, the catheter comprising:

a catheter body having a proximal end and a distal end, the body containing an angioplasty pressurization lumen, a cryogenic fluid supply lumen, and a cryogenic fluid exhaust lumen;

an angioplasty balloon disposed near the distal end of the body, the angioplasty balloon in fluid communication with the pressurization lumen and capable of dilating the diseased vessel wall when the angioplasty balloon is pressurized within the blood vessel;

a cryogenic balloon disposed near the distal end of the body, the cryogenic balloon in fluid communication with the exhaust lumen; and a diffuser having a plurality of cryogenic fluid ports disposed within the cryogenic balloon, the supply lumen in fluid communication with the balloon through the diffuser so that cryogenic fluid from the supply lumen is distributed within the balloon by the diffuser.

26. The catheter of claim 25, wherein the catheter body further defines a guidewire lumen, the guidewire lumen extending distally of the angioplasty balloon and the cryogenic balloon.

27. The catheter of claim 26, wherein the diffuser comprises an axially oriented tube having a plurality of perforations.

28. The catheter of claim 27, wherein the guidewire lumen extends axially through the diffuser tube.

* * * * *